US009457106B2

(12) United States Patent
Knox

(10) Patent No.: US 9,457,106 B2
(45) Date of Patent: Oct. 4, 2016

(54) CANCER THERAPY

(76) Inventor: Peter Knox, Wantage (GB)

( * ) Notice: Subject to any disclaimer, the term of this patent is extended or adjusted under 35 U.S.C. 154(b) by 0 days.

(21) Appl. No.: 14/112,797

(22) PCT Filed: Apr. 18, 2012

(86) PCT No.: PCT/GB2012/050852
§ 371 (c)(1),
(2), (4) Date: Jan. 29, 2014

(87) PCT Pub. No.: WO2012/143713
PCT Pub. Date: Oct. 26, 2012

(65) Prior Publication Data
US 2014/0134104 A1 May 15, 2014

(30) Foreign Application Priority Data
Apr. 19, 2011 (GB) .................................. 1106630.5

(51) Int. Cl.
A61K 51/00 (2006.01)
A61M 36/14 (2006.01)
A61K 51/02 (2006.01)
A61K 51/12 (2006.01)

(52) U.S. Cl.
CPC .............. *A61K 51/02* (2013.01); *A61K 51/025* (2013.01); *A61K 51/121* (2013.01)

(58) Field of Classification Search
CPC .. A61K 2121/00; A61K 51/00; A61K 51/02; A61K 51/025; A61K 51/0497; A61K 51/04; A61K 51/0493; A61K 51/121

USPC ............ 424/1.11, 1.61, 1.77, 9.1, 9.2, 1.81; 514/1
See application file for complete search history.

(56) References Cited

U.S. PATENT DOCUMENTS 4,416,865 A * 11/1983 Rhodes et al. ............... 424/1.69
6,352,682 B2 * 3/2002 Leavitt et al. ............... 424/1.25

FOREIGN PATENT DOCUMENTS

| FR | 2667244 A1 | 4/1992 |
|----|------------|--------|
| WO | WO-99/22775 A1 | 5/1999 |
| WO | WO-2005/023316 A1 | 3/2005 |
| WO | WO-2007/008232 A2 | 1/2007 |
| WO | WO-2009/045230 A1 | 4/2009 |

OTHER PUBLICATIONS

International Preliminary Report on Patentability for PCT/GB2012/050852, 4 pages (May 21, 2013).
International Search Report for PCT/GB2012/050852, 4 pages (Dec. 5, 2012).
McCready, V.R. and Cornes, P., The potential of intratumoural unsealed radioactive source therapy, European Journal of Nuclear Medicine, 28(5): 567-569 (2001).
Written Opinion for PCT/GB2012/050852, 5 pages (Dec. 5, 2012).

* cited by examiner

*Primary Examiner* — D L Jones
(74) *Attorney, Agent, or Firm* — Choate, Hall & Stewart LLP; Charles E. Lyon; David E. Shore

(57) ABSTRACT

The invention provides a method of treating a tumor or other lesion comprising introducing a solution comprising one or more radioactive isotopes directly into said tumor or other lesion in a mammal to effect in situ precipitation of a radioactive precipitate in the tumor or other lesion.

10 Claims, 3 Drawing Sheets

Microscopic visualization at site of injection

View at 5 minutes       View at 1 hour

CANCER THERAPY

CROSS-REFERENCE TO RELATED APPLICATIONS

This application claims priority to International Application Number PCT/GB2012/050852, filed on Apr. 18, 2012, which claims priority to United Kingdom Patent Application serial number 1106630.5, Apr. 19, 2011, the entirety of each of which is incorporated herein by reference.

TECHNICAL FIELD

The present invention relates to a method of cancer therapy. In particular, the present invention relates to the introduction of a solution comprising one or more radioactive isotopes into a tumour mass in the body of a mammal to effect in situ precipitation in the tumour. The radioactive precipitate will provide a therapeutic benefit.

BACKGROUND

The development of new and improved methods for the treatment of cancer and palliation of the symptoms associated with cancer is of huge importance.

Common cancer therapies include the use of chemotherapeutic agents which are delivered systemically and have little or no tumour specificity, which results in the potential for harm to healthy organs in the body and causes symptoms such as myelosuppression, mucositis and alopecia.

Various forms of radiation are toxic to mammalian cells and have been harnessed successfully for the treatment of cancer. Radioactive isotopes have been used to treat certain cancers, for example cancers of the thyroid and prostate. Such therapies have also been employed for the treatment of disorders such as polycythemia vera. However, for logistical reasons including the considerable expense of suitable radiation delivery systems, radiation therapy is used less frequently than would otherwise be desirable.

Fractionation (and hypofractionation) methods have also been used in the treatment of cancer. These methods increase the likelihood of tumour cells being targeted during a phase of the cell cycle in which they are susceptible to radiation, rather than employing a single "dose" of radiation which may only interact with tumour cells at a phase of the cell cycle where the target cells are relatively resistant to radiation. Optimizing the potency of such techniques is the subject of much discussion in the field (see e.g. Yarnold, J., Bentzen, S. M., Coles, C., Haviland, J., *Int. J. Radiat. Oncol. Biol. Phys.*, 2011, 79(1), 1). Brachytherapy techniques, such as the implantation into a tumour of solid radioactive "seeds", which ensure a continuous source of radiation, have been used successfully in the treatment of prostate cancer (see e.g. Taira, A. V., Merrick, G. S., Butler, W. M., Galbreath, R. W., Lief, J., Adamovich, E., and Wallner, K. E., *Int. J. Rad. Oncol.*, 2011, 79, 1336). However, the delivery of solid "seeds" into the appropriate area requiring treatment can be problematic.

Another established method in the field of oncology is embolization, i.e. the occlusion of blood vessels within a tumour to bring about a therapeutic benefit. Artificial emboli such as platinum coils or inflatable balloons are common. Furthermore, liquid embolic agents have been developed, including n-butyl-2-cyanoacrylate (Enbucrilate), which polymerizes upon contact with moisture, blood and/or tissue forming a glue to obstruct blood vessels.

However, there remains a need for further minimally invasive methods by which a wide range of tumours or other lesions may be targeted in a selective, predictable and efficient manner in order to achieve palliation of symptoms or destruction of all or part of the mass of a tumour or other lesion. This includes a need for improved ways of harnessing radioactive isotopes for use in such therapies.

DISCLOSURE OF THE INVENTION

The inventor has devised a new method of cancer therapy. In one aspect of the invention is provided a method of treating a tumour or other lesion comprising introducing a solution comprising one or more radioactive isotopes directly into said tumour or other lesion in a mammal to effect in situ precipitation of a radioactive precipitate in said tumour or other lesion.

The solution being introduced will be a homogeneous mixture of two or more substances and is typically an aqueous or aqueous buffered solution. The solution preferably comprises phosphate ions, such as phosphate buffered saline. It will be understood that the term "phosphate ions" may be used to describe the phosphate ion $PO_4^{3-}$, the hydrogen phosphate ion $HPO_4^{2-}$, and the dihydrogen phosphate ion $H_2PO_4^{-}$, one or more of which may be comprised in the solution being introduced in the methods of the present invention. The form of the phosphate ion will, of course, be dependent on the pH of the environment. In the methods of the present invention, the pH of the solution being introduced will be greater than 6. Suitably the pH of the solution will be between 7 and 8. Preferably, the pH of the solution will be between 7.0 and 7.6. Most preferably the pH of the solution will be 7.4.

The concentration of the phosphate solution being introduced will usually be from 50 to 200 mM. Preferably the concentration of phosphate solution being introduced will be between 50 and 100 mM, more preferably between 50 and 75 mM. The solution will usually be injected into the tumour or other lesion over a period of between 5 seconds and 10 seconds. The solution will comprise one or more radioactive isotopes, i.e. it will comprise one or more radioactive isotopes which when delivered at a suitable concentration into a tumour or other lesion effects the formation of a radioactive precipitate within the tumour or other lesion with one or more endogenous counter-ions. The inventor has found that these methods may provide advantages compared to the glue methods of the prior art (described above).

The precipitate may comprise solid particles, a microscopic dispersion such as colloids, or a heterogeneous fluid containing solid particles such as a suspension. The precipitate may also comprise an immobilized gel. The precipitate may comprise inorganic minerals, such as calcium salts. The affected region of the body requiring therapy will usually be a tumour or lesion. The use of the methods of the invention may lead to alleviation of one or more symptoms associated with the tumour or other lesion or to the destruction of all or part of the mass of the tumour or other lesion. The method may be used in the treatment of cancer, for example pancreatic cancer, colorectal cancer, lung cancer, prostate cancer, breast cancer, or cancers of the head or neck which are particularly difficult to treat using conventional methods. The method may be used to treat metastatic nodules. The method may be used in the treatment of brain tumours.

The therapy relies on the ability of a radioactive precipitate to disrupt the normal functioning of cells, causing death of cancer cells and thus providing a therapeutic benefit.

The inventor has observed that the formation of a precipitate of, for example, calcium phosphate, causes a thrombogenic effect and thus represents a new method of embolization which had not been predicted until experiments were performed. Blood clots form in the area being treated and the formation of such clots in accelerated markedly by the presence of crystal particles. This embolization in combination with the destructive nature of the radioactive isotopes on target cancer cells represents a complementary means by which the cancer cells are destroyed. Given the embolisation is a well established treatment that is known to be effective in oncology this represents a further advantage of the invention which had not been predicted until experiments were performed.

An example within the terms of the present invention is thus a radioactive phosphate solution which is able to form a precipitate with endogenous calcium in tissue, resulting in a therapeutic precipitate in the desired area. Thus, in one embodiment, the therapeutic precipitate comprises calcium. In another embodiment, the therapeutic precipitate also comprises phosphate. Specifically, in a preferred embodiment, a radioactive precipitate will form as follows:

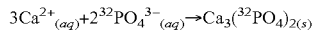

$$3Ca^{2+}_{(aq)} + 2\,^{32}PO_4^{3-}_{(aq)} \rightarrow Ca_3(^{32}PO_4)_{2(s)}$$

where (aq) denotes that the ions are dissolved in water and (s) denotes that the substance is in the solid phase. The solubility product, $K_{sp}$, of calcium phosphate is $2.07\times10^{-31}$ (at 25° C.). The skilled person will be aware that solubility coefficients and thus the conditions at which a precipitate will form are highly dependent on local conditions in vivo such as pH, protein concentration and temperature. Thus, the skilled person will understand that it is preferable to use a solution that will precipitate under physiological conditions, such as disodium hydrogen phosphate. Alternatively, it may be necessary to introduce additional counter-ions to the solution in order for precipitation to be effected under physiological conditions. For example, sulphate or hydroxyl counter-ions may assist precipitation.

Even altering the source of water when measuring solubility product values can have a significant effect. In one embodiment, the solubility product, $K_{sp}$, of the precipitate will be less than $10^{-25}$. For instance, the solubility product of the precipitate may be less than $10^{-26}$, optionally less than $10^{-27}$, optionally less than $10^{-28}$, or optionally less than $10^{-29}$. In a preferred embodiment, the solubility product is less than $10^{-30}$. The suitability of a precipitate for use in the methods of the present invention may also be assessed by reference to solubility (expressed in, for example, mg/L). In one embodiment, a suitable precipitate will have a solubility in water (at 25° C.) of less than 100 mg/L. For instance, the precipitate may have a solubility in water (at 25° C.) of less than 80 mg/L, or optionally less than 60 mg/L. In a preferred embodiment, the precipitate will have a solubility in water (at 25° C.) of less than 40 mg/L.

Furthermore, although the above reaction scheme describes a solid precipitate comprising solely calcium and phosphate ions, it will be understood that in practice the therapeutic precipitate will comprise various insoluble complexes, such as calcium hydrogen phosphate. It may also be possible to precipitate the phosphate ions using a different system, such as insoluble hydroxides.

Other examples of solutions that form precipitates with endogenous counter-ions under physiological conditions will be clear to those of skill in the art. Thus, the skilled person would have no difficulty in identifying suitable counter-ions, particularly by reference to known solubility parameters and the methods described in the present specification.

Radioactive isotopes dissipate energy upon return to a ground state and, in doing so, interact with water and other cellular components causing damage to, for example, tumour cells. Typically, radiation therapies utilize ionizing radiation, whereby the energy of the radiation is sufficient to eject an orbital electron from an atom upon interaction. The ionization potential of most biological molecules is between about 10 to 15 eV. All types of radiation capable of producing such energy are therefore deemed to be "ionizing radiation". Such types of radiation include X-rays, gamma rays and particulate radiation such as protons, neutrons and alpha particles.

However, the form and dosage regime of radiation that is appropriate in any given therapy depends on the type, stage and size of the tumour. For example, tissues exhibiting a higher proliferative capacity are often more sensitive to radiation than those with a lower proliferative capacity. Often, an "N-factor" is used to quantify the degree of sensitivity to radiation. For example, the gonads have the highest N-factor of any human tissue with a value of 0.20 and are thus most sensitive to radiation. Other tissues which have high rates of cellular proliferation such as bone marrow and intestines have an N-factor of around 0.12, while relatively inert tissue such as bone has an N-factor of 0.01.

There are a number of parameters of relevance when considering how to optimize the therapeutic effect achieved by radiotherapy. Quality factor, Q, is a dimensionless parameter that is useful when considering the effect of various forms of radiation on tissue. The value of Q depends on the linear energy transfer (LET) and relative biological effectiveness (RBE) of the radiation. In water, the quality factor of photons and electrons is unity whereas an alpha particle has a quality factor of twenty. Accordingly, an alpha particle will be very damaging to tissue but will dissipate its energy over a very short distance.

Linear energy transfer (LET) is a measure of the energy transferred to a material as an ionizing particle passes through it. LET is used frequently to quantify the effects of ionizing radiation on biological specimens. Typical LET values for various types of radiation are as follows:

X-rays and gamma rays~0.3 kev/micron
beta particles~5 to 100s kev/micron
alpha particles~100s kev/micron
fission products~1000s kev/micron As LET increases, so too does the amount of energy that is dissipated per unit distance. It is important that this parameter is considered to ensure that the majority of energy is dissipated within the area requiring treatment, such as the tumour or other lesion, i.e. to maximize the toxic effect at the desired area while minimizing the damage to healthy cells in the surrounding area. If the LET were too high, the excited particle or wave would pass out of the body without dissipation of energy. It should be noted that a beta particle will deposit its energy in a one-part process.

Relative biological effectiveness (RBE) is based on the concept that different types of radiation interact with living organisms differently. RBE is given as the dose of a reference radiation, usually X-rays, required to produce the same biological effect as that achieved using a test dose of another radiation.

In order to achieve optimal decay profiles in the methods of the present invention (i.e. to focus dissipation of energy within the area requiring therapy), it may be necessary to combine different radioactive isotopes. Different radioactive isotopes emit radiation with different energy profiles and, thus, the use of more than one radioactive isotope may lead to an improved cytotoxic effect. For example, certain emissions will not be sufficiently energetic to penetrate to the periphery of a large tumour mass and therefore a combination of isotopes with differing energy profiles would be required to facilitate energy deposition throughout the tumour or lesion. A combination of samarium-153 and yttrium-90 has been found to be effective. The ratio of each radioisotope that would be used to target a particular tumour would depend on the size of the tumour and the number of injection sites that are practicable.

Alternatively, the use of one radioactive isotope may be sufficient to bring about a significant therapeutic effect. It will, however, be appreciated that the majority of radioactive isotopes emit a combination of waves and particles upon decay. A common combination would be that of a beta particle and a gamma wave.

In one embodiment, at least one of the one or more radioactive isotopes decays principally by beta decay. For instance, the one or more radioactive isotopes may be selected from iodine-131, phosphorus-32, phosphorus-33, strontium-89, samarium-153, yttrium-90, ruthenium-103. Phosphorus-32 is particularly preferred.

In one embodiment, at least one of the one or more radioactive isotopes decays principally by electron capture decay. For instance, the one or more radioactive isotopes may be selected from iodine-125 and palladium-103.

An iodine-125 solution may be too soluble to effect precipitation when introduced to the region of the body requiring therapy. Nevertheless, co-administration with a solution that does form a precipitate in the body will 'trap' the radioactive iodine-125 in the area requiring therapy, thus preventing leaching of the radioactive solution from the desired area. Such a solution may either be radioactive ("hot") or non-radioactive ("cold"). An example of a "hot" solution would be a phosphate solution comprising phosphorus-32 of appropriate concentration. Here, both the radioactive phosphate (i.e. phosphate containing phosphorus-32) and the iodine-125 will be confined to the region of the body requiring treatment by virtue of the precipitate formed with the phosphate. A solution of yttrium-90 may also be suitable for use in such a method. A "cold" phosphate solution is an example of a suitable non-radioactive solution. Other "cold" solutions comprising non-radioactive isotopes capable of forming a precipitate with endogenous counterions would also be suitable. It may also be possible to use more than one solution, either "hot", "cold", or a combination thereof.

In one embodiment, at least one of the one or more radioactive isotopes decays principally by gamma decay.

In one embodiment, the solution comprises a combination of radioactive isotopes. The combination may comprise principally radioactive isotopes that decay by beta decay, by electron capture decay or by gamma decay, or any combination thereof. This enables a combination of isotopes with differing energy profiles to facilitate energy deposition across a tumour mass in its entirety.

Certain radioactive isotopes may be preferred depending on the specific tumour or other lesion. For example, radioactive strontium chloride is used to treat bone metastases because strontium is a calcium mimetic and therefore affects osteoblasts, which have a high calcium uptake, particularly at the epiphyses. An example within the terms of the present invention is thus a phosphate solution comprising radioactive phosphorus-32 which is able to form a precipitate with endogenous calcium in tissue, resulting in a therapeutic precipitate in the desired area Another important consideration when selecting which radioactive isotope to use against a particular tumour is the energy and half-life of the isotope. For example, phosphorus-32 has a maximum beta-particle energy of 1.71 MeV and a half-life of approximately 14 days, which means that a single dose will be of therapeutic benefit for a relatively long period of time (although not too long). The persistence of energy dissipation by an element such as phosphorus-32 is important in therapy, since it maximizes the probability that energy will be dissipated at an appropriate stage of the cell cycle such that cell death occurs upon interaction and preferably over the cell division period. Fractionation techniques have been used successfully where conventional radiation techniques have been less successful, due in part to the increased likelihood of an excited particle or wave interacting with a cell at a stage of the cell cycle such that death of the cell results.

The energies and half-lives of a number of beta particles (see above for phosphorus-32) are as follows:

| Radioisotope | Maximum particle energy/MeV | Half-life |
| --- | --- | --- |
| iodine-131 | 0.61 | 8.04 days |
| strontium-89 | 1.46 | 51 days |
| samarium-153 | 0.7 (>50%) | 47 hours |
| yttrium-90 | 2.27 | 64.2 hours |
| ruthenium-103 | 0.214 MeV | 40 days |

The energies and half-lives of two electron capture emitters are as follows:

| Radioisotope | Particle energy/MeV | Half-life |
| --- | --- | --- |
| iodine-125 | 0.035 | 60 days |
| palladium-103 | 0.05 | 17 days |

As described above, the introduction into a tumour or other lesion of a solution comprising, for example, radioactive phosphate ions of a certain concentration will cause a radioactive precipitate of calcium phosphate to form. In one embodiment, the solution comprises radioactive phosphorus-32 and thus the resulting precipitate will comprise $Ca_3(^{32}PO_4)_2$ $_{(s)}$. Optionally, the method will further comprise co-administration of a solution comprising calcium. In one embodiment, the method will further comprise co-administration of a chelating agent. The chelating agent may be ethylene glycol tetraacetic acid (EGTA), ethylenediaminetetraacetic acid (EDTA) or any other suitable chelator of cations. Preferably, the chelating agent is ethylene glycol tetraacetic acid (EGTA).

When the radioactive solution comprises phosphorus-32, the radioactive isotope will normally be introduced into the tumour or other lesion at a level of from 0.1 to 2 MBq per cubic centimeter of tumour or other lesion, or preferably at a level of from 0.2 to 0.8 MBq per cubic centimeter of tumour or other lesion. The required specific activity will be achieved by mixing the radioactive phosphate solution with non-radioactive phosphate solution. The adjustment of specific activity will also allow the introduction of different volumes of solution into the tumour or other lesion in order to achieve the desired dose of radiation. It is important to note that the specific activity of a particular sample of radioisotope is provided by the manufacturer based on the specific activity of the sample shortly after formation of the radioisotope, which will often be a number of days prior to use in the methods of the invention. Thus, the specific activity cited by the manufacturer will be higher than the actual specific activity at the time of dilution for use in the present methods. However, the skilled person would be able to calculate the actual specific activity of the sample at a given time based on the data provided by the manufacturer (i.e. the specific activity at a certain time) and known decay characteristics of the radioisotope in question.

The volume of solution to be introduced into the tumour or other lesion is typically between 3 and 20% of the volume of the tumour or other lesion. In a preferred embodiment, the volume of solution to be introduced into the tumour or other lesion is 10% of the volume of the tumour or other lesion.

Thus, for a tumour or other lesion of 1 cm$^3$, it would be appropriate to introduce, for example, 0.03 to 0.2 cm$^3$, preferably 0.1 cm$^3$ of solution having an activity of from 0.1 to 2 MBq. For a tumour or other lesion of 5 cm$^3$, it would be appropriate to introduce, for example, 0.15 to 1.0 cm$^3$, preferably 0.5 cm$^3$ of solution having an activity of from 0.5 to 10 MBq. For a tumour or other lesion of 10 cm$^3$, it would be appropriate to introduce, for example, 0.3 to 2.0 cm$^3$, preferably 1.0 cm$^3$ of solution having an activity of from 1.0 to 20 MBq. For a tumour or other lesion of 20 cm$^3$, it would be appropriate to introduce, for example, 0.6 to 4.0 cm$^3$, preferably 2.0 cm$^3$ of solution having an activity of from 2.0 to 40 MBq. For a tumour or other lesion of 50 cm$^3$, it would be appropriate to introduce, for example, 1.5 to 10 cm$^3$, preferably 5.0 cm$^3$ of solution having an activity of from 5.0 to 100 MBq. Clearly, with the understanding of the present invention the skilled reader will be able to calculate appropriate volumes and doses.

The radioactive emissions from phosphorus-32 in the calcium phosphate precipitate will dissipate their energy within the area requiring therapy, resulting in a therapeutic effect which may be complemented by the embolization methods described above. Examples of other suitable radioactive isotopes include yttrium-90 and strontium-89, which when introduced in solution to the region to be treated at a suitable concentration would effect the formation of therapeutic precipitates with endogenous sulphate ions, i.e. yttrium sulphate and strontium sulphate.

In order to shift the equilibrium to such an extent that a precipitate is formed, it will be necessary to have a solution containing phosphate ions in excess of a certain concentration. In other words, taking phosphate as the example in this instance, there must be sufficient phosphate to shift the solubility equilibrium via the common ion effect thus forming a precipitate of calcium phosphate in the tumour or other lesion. Once formed, the calcium phosphate precipitate will be very stable and, therefore, there will be little or no spread of radioactive phosphate ions into healthy tissue in the areas surrounding the tumour.

Ionized calcium ($Ca^{2+}_{(aq)}$) is present in extracellular fluid at a concentration in the order of $10^{-3}$ M. As mentioned above, calcium phosphate has a solubility product, $K_{sp}$, of $2.07 \times 10^{-31}$. Since $$K_{sp} = ([Ca^{2+}_{(aq)}]^3)([PO_4^{3-}_{(aq)}]^2) / [Ca_3(PO_4)_{2(s)}]$$
$$= ([Ca^{2+}_{(aq)}]^3)([PO_4^{3-}_{(aq)}]^2)$$

it follows that, at equilibrium, the concentration of ionized phosphate ($PO_4^{3-}_{(aq)}$) in the extracellular fluid will be in the order of $10^{-11}$ M.

Thus, when the concentration of phosphate is greater than about $10^{-11}$ M, the equilibrium will be shifted such that a precipitate of calcium phosphate forms. It is therefore possible to inject a solution of phosphate at a concentration and amount such that substantially all of the phosphate is precipitated in the tumour or other lesion but not outside it i.e. the concentration of aqueous phosphate at the perimeter of the tumour or other lesion will be less than about $10^{-11}$ M and thus no precipitate will be formed outside the tumour or other lesion.

It should be noted that although the total concentration of physiological calcium ions is actually about 2.5 mM, about 1.5 mM of these calcium ions (divalent cations) are bound to proteins (principally to amino acid hydroxyl and carboxylic acid groups) within the body, hence a concentration of "free" calcium ions of around 1.0 mM (as used in the calculation above). The skilled person would be aware that some of the calcium ions that are bound to proteins may become available to form a precipitate with the aqueous phosphate since the dissociation constant for the binding of calcium to protein is not particularly high.

To achieve the requisite concentration of phosphate ions it is necessary to reduce massively the specific activity of the radioactive phosphorus-32 by mixing it with a non-radioactive form of the same element, i.e. with a phosphate solution comprising phosphorus-31. At a phosphate concentration of about $10^{-11}$ M or less (i.e. at a concentration where no precipitate is formed in vivo and at which concentration the phosphate will not be confined to the target area), the amount of radioactive phosphorus-32 will therefore be minuscule and will pose no risk to the health of the patient. In the present invention, substantially all phosphorus-32 is confined to the precipitate in the area requiring treatment. Failure to dilute the radioactive phosphate with non-radioactive phosphate could be compensated for either by injection of a very small amount of solution such that a precipitate would form within a very small volume, or by injection of a very dilute phosphate solution resulting in leaching of radioactive phosphorus-32 throughout the body, which would be undesirable.

Thus, according to the invention the specific activity of the one or more radioactive isotopes is reduced by mixing the solution comprising the one or more radioactive isotopes with a solution comprising non-radioactive isotopes of the same chemical element or elements. The specific activity of the solution being introduced to the tumour should be calculated based on a number of factors, including the size and type of the tumour.

The solution may be introduced to the tumour or other lesion by means of a needle and catheter system. The solution may be introduced by trans-epithelial or intra-cavity injection. The method of introducing the solution may be accompanied by the use of an ultrasound probe or stereotactic apparatus to assist entry. The delivery system may comprise a shielding device in order to protect the operator from exposure to radiation. The radioactive solution may be delivered to one or more sites within the tumour or other lesion.

The region of the body to be treated may be located using a clinical imaging technique such as a computed tomography scan, a magnetic resonance scan, nuclear imaging including SPECT and ultrasound imaging. In some cases it may be appropriate to use more than one technique to enable images to be superimposed, giving a precise three-dimensional image which can be used to calculate the volume and margins of the tumour or lesion. An algorithm may then be applied to assist in the definition of the volume and margins of the region requiring treatment, which will be useful in determining an optimal treatment regime.

The method may be preceded, followed, or accompanied by hormone ablation therapy, particularly in the treatment of prostate and breast tumours. In the case of prostate tumours, such therapy would lower the level of testosterone, while for breast tumours such therapy would lower the levels of oestrogen and progesterone.

In the description above, features related to one aspect of the invention are also, where applicable, features of the other aspects of the invention. It will be recognised that features specified in one embodiment of the invention may be combined with other specified features to provide further embodiments.

The invention will now be described with reference to examples. It will be appreciated by the skilled reader that strict adherence to the terms of the examples is not necessary, and thus variation around the described themes is intended.

EXAMPLES

All phosphate buffered solutions were prepared according to the methods devised by Sorensen (modified by Gomori), as described in *Methods of Enzymology*, 1955, 1, 143.

Precipitation of "Cold" Calcium Phosphate

Aqueous solutions of calcium chloride at various concentrations were prepared.

Samples of the solutions were taken and mixed with an equal volume of a solution of 100 mM disodium hydrogen phosphate, buffered to pH 7.4, yielding a suspension comprising solid calcium phosphate.

Figure 1:
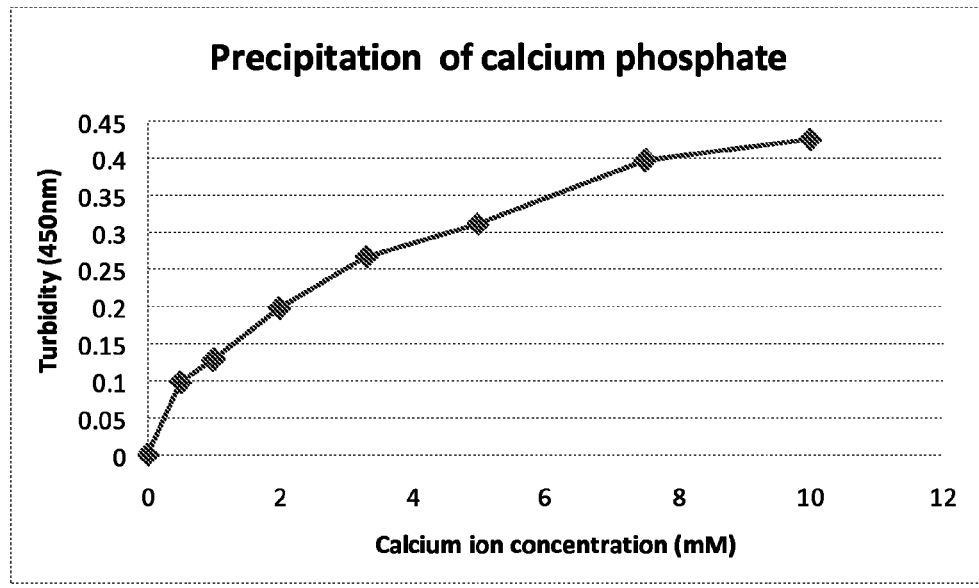
FIG. 1 shows the turbidity of a series of suspensions comprising solid calcium phosphate upon mixing 100 mM disodium hydrogen phosphate with a solution of calcium chloride, as a function of the concentration of calcium ions in the solution of calcium chloride.

The turbidity of each of the resulting suspensions was measured using a spectrophotometer at 450 nm, as shown in Table 1 and FIG. 1. Microscopic examination of the suspensions revealed the formation of an inhomogeneous range of crystal shapes and sizes depending on the concentration of the calcium chloride solution.

TABLE 1

| Concentration of calcium ions (mM) | Turbidity |
|---|---|
| 0 | 0 |
| 0.5 | 0.098 |
| 1 | 0.127 |
| 2 | 0.196 |
| 3.3 | 0.267 |
| 5 | 0.310 |
| 7.5 | 0.397 |
| 10 | 0.426 |

Precipitation of "Hot" Calcium Phosphate

Phosphate solutions comprising phosphorus-32 or phosphorus-33 were prepared at a range of specific activities. These solutions were mixed with an equal volume of a solution of 1.5 mM calcium chloride.

The resulting filtrates and precipitates (after re-suspension in distilled water) were analysed to determine levels of radiation. For the samples containing phosphorus-32, Cherenkov radiation was measured. For the samples containing phosphorus-33, scintillation proximity assays were carried out.

Figure 2:
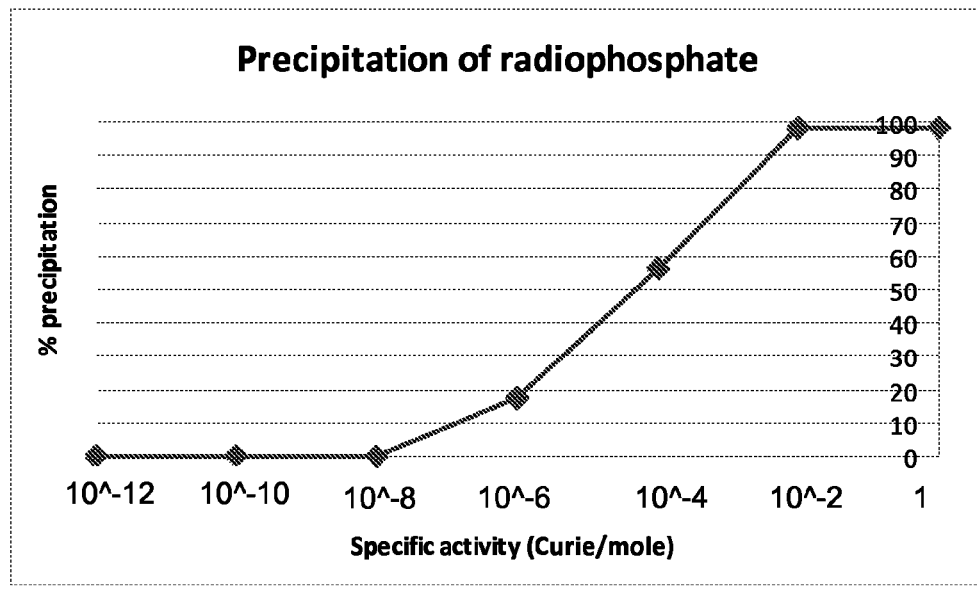
FIG. 2 shows the percentage of radioactive phosphate from a series of solutions comprising phosphorus-32 or phosphorus-33 that forms a precipitate upon mixing with an equal volume of a solution of 1.5 mM calcium chloride as a function of the specific activity of each solution comprising phosphorus-32 or phosphorus-33.

Table 2 shows the percentage of each solution that was precipitated as a function of specific activity (see also FIG. 2).

TABLE 2

| Specific activity (Curie/mole) | Radiophosphate precipitated (%) |
|---|---|
| 1 | 98 |
| $10^{-2}$ | 98 |
| $10^{-4}$ | 56 |
| $10^{-6}$ | 17 |
| $10^{-8}$ | 0 |
| $10^{-10}$ | 0 |
| $10^{-12}$ | 0 |

Microscopic Visualization of Precipitates at the Site of Injection

Disodium hydrogen phosphate solutions were mixed with a small volume of Patent Blue dye, in order to visualize the diffusion of the solution following injection into tissue. Patent Blue dye has been used previously in medicine, for example in the location of lymphatic vessels during lymphangiography.

Using a 25 g needle, solutions of disodium hydrogen phosphate and Patent Blue dye were delivered in vitro into organ tissues including skin, muscle and nervous tissue. Following injection, the tissues were viewed using bright-field and phase contrast microscopy.

Figure 3:
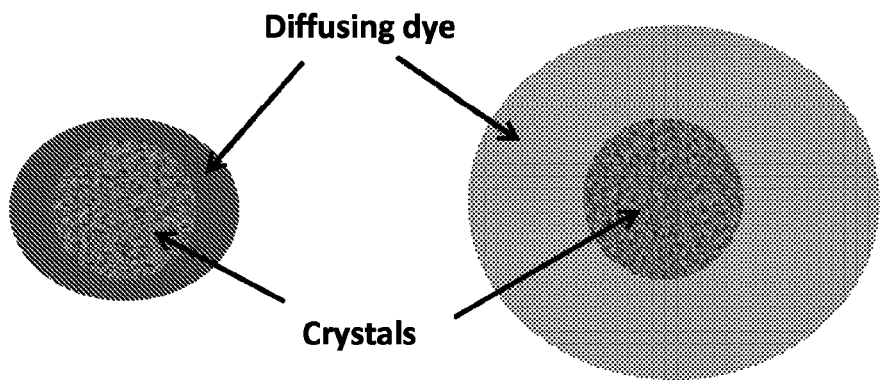
FIG. 3 shows a schematic representation of the diffusion of a solution of disodium hydrogen phosphate mixed with Patent Blue dye following injection into tissue (at 5 minutes after injection and at 1 hour after injection).

In each case, the Patent Blue solution diffused into the tissue with time, whereas the crystals (containing calcium and phosphate ions) remained substantially at the site of injection. This phenomenon is shown schematically in FIG. 3.

Effect of Calcium Phosphate on Blood Coagulation

The inventor has found that, following injection of phosphate solution, microthrombi are formed at the site of precipitation of calcium phosphate. Studies have been carried out to investigate the rates of thrombogenesis in the presence of calcium phosphate crystals. Human blood was drawn from an antecubital vein and was chilled rapidly, using the technique described in Knox, P., and Crooks, S., *J. Cell. Physiol.*, 1988, 135, 467. The chilled blood was placed in plastic containers to hinder the clotting process. Clotting can be stimulated using a pre-coagulant material and/or raising the temperature.

A suspension of calcium phosphate was prepared by mixing equal volumes of calcium chloride (100 mM) and disodium hydrogen phosphate (100 mM) solutions. The resulting suspension was centrifuged and the precipitate was washed in distilled water. The precipitate was then re-suspended in isotonic saline solution.

Different volumes of the re-suspended calcium phosphate solution were added to aliquots of the chilled human blood and the samples were brought to room temperature. The amount of material that had coagulated and the amount of residual fluid was measured at 15 and 45 minutes following the addition of the re-suspended solution in the blood samples.

Figure 4:
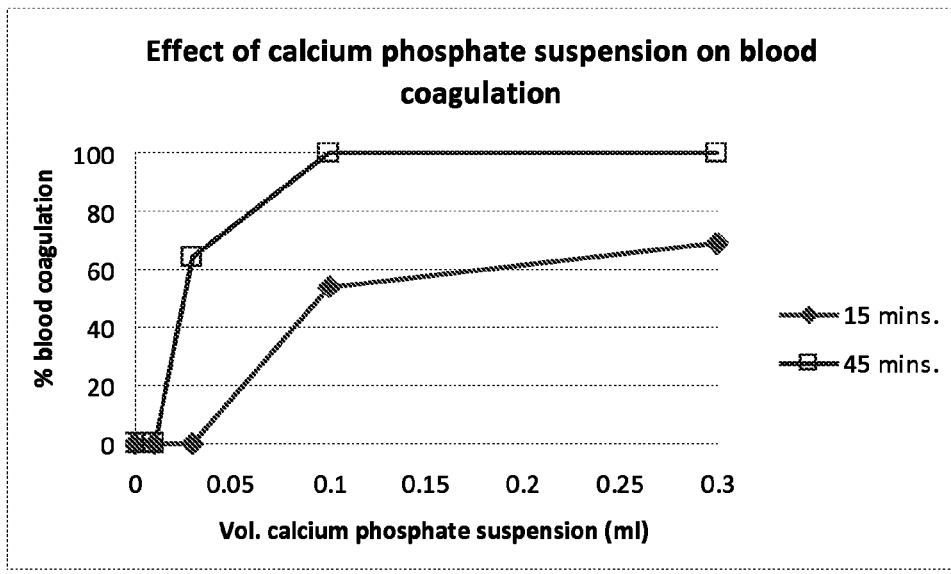
FIG. 4 shows the amount of human blood that had coagulated and the amount of residual fluid at 15 and 45 minutes following the addition of chilled human blood to a solution of re-suspended calcium phosphate, as a function of the volume of calcium phosphate solution.

Table 4 and FIG. 4 show the amount of coagulant (wt % as a percentage of the total weight of the sample) at 15 and 45 minutes following the addition of the re-suspended solution into the blood samples as a function of the volume of re-suspended calcium phosphate solution added to the blood. It is important to note that no clotting would be expected at 45 minutes under normal conditions (i.e. in the absence of crystals).

pH Studies

The inventor has carried out experiments which confirm the significant extent to which pH conditions influence the formation of a precipitate with any given solution. At physiological conditions, the addition of 1 mL of calcium chloride solution (50 mM) to 10 mL disodium hydrogen phosphate (100 mM) effected formation of a heavy visible precipitate. In contrast, when 1 mL of calcium chloride solution (50 mM) was added to 10 mL sodium dihydrogen phosphate (100 mM), no precipitate was formed (i.e. the solution remained clear).

Figure 5:
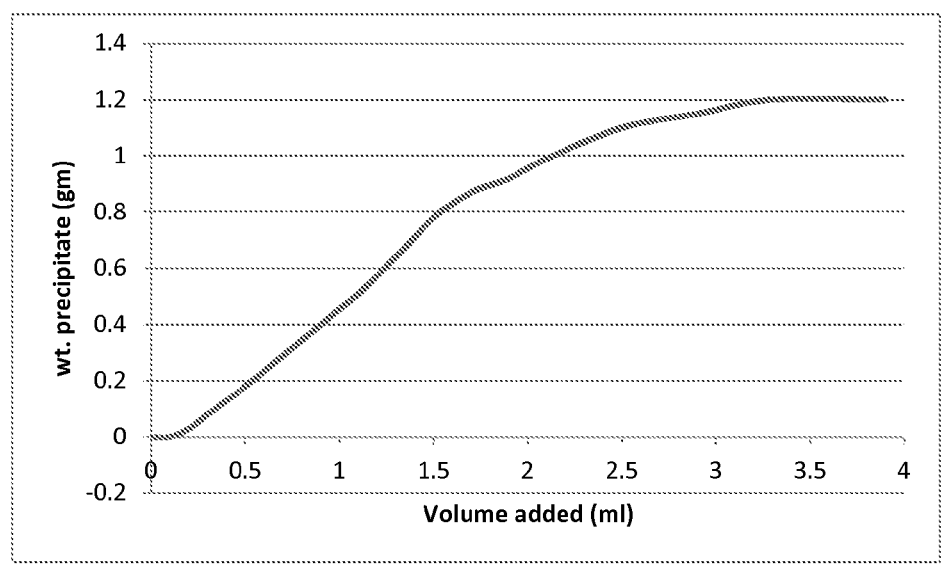
FIG. 5 shows the amount of calcium phosphate precipitate formed from a solution containing 50 mL of sodium dihydrogen phosphate (100 mM) and 5 mL of calcium chloride (50 mM) as a function of the amount of sodium hydroxide (0.05 M) added.

FIG. 5 shows the amount of precipitate formed from a solution containing 50 mL of sodium dihydrogen phosphate (100 mM) and 5 mL of calcium chloride (50 mM) as a function of the amount of sodium hydroxide (0.05 M) added. This shows that as the solution of sodium dihydrogen phosphate (which is acidic in the absence of sodium hydroxide) approaches neutral pH, a precipitate of calcium phosphate begins to form.

These studies confirm that it is important to select a solution that will precipitate under physiological conditions for use in the present invention or, alternatively, to introduce additional counter-ions to the solution in order for precipitation to be effected under such conditions.

Theoretical Therapeutic Example

A patient requires treatment for a breast tumour with a volume of 20 cm$^3$. The tumour should be located using a magnetic resonance scan and an algorithm applied to assist in definition of the volume and margins of the tumour and thus the selection of a suitable treatment regime.

Using a needle and catheter system and guided by an ultrasound probe (or using stereotactic apparatus), 2 cm$^3$ of phosphate solution of activity 10 MBq should be injected into the tumour mass to effect precipitation of radioactive calcium phosphate within the breast tumour. A shielding device should be used during delivery of the solution to protect the operator from exposure to radiation.

The invention claimed is:

1. A method of treating a tumor comprising introducing a solution comprising radioactive phosphate ions directly into said tumor in a mammal to effect in situ precipitation of a radioactive precipitate comprising calcium phosphate in said tumor, wherein:
   the radioactive phosphate ions comprise phosphorous-32 or phosphorous-33;
   said radioactive phosphate ions interact with endogenous calcium to form said radioactive precipitate; and
   said radioactive precipitate causes cell death and treats the tumor.

2. The method according to claim 1, wherein the solution further comprises non-radioactive phosphate ions.

3. The method according to claim 1, further comprising the step of introducing a second solution comprising one or more different radioactive isotopes into said tumor, wherein said second solution does not form a precipitate in situ but is entrapped within said tumor by the radioactive precipitate.

4. The method according to claim 1, further comprising the step of co-administering a solution comprising calcium.

5. The method according to claim 1, further comprising the step of co-administration of a chelating agent.

6. The method according to claim 1, wherein the solution is introduced into the tumor by means of a catheter, optionally via trans-epithelial or intra-cavity injection.

7. The method according to claim 1, wherein the introduction of the solution into the tumor is accompanied by the use of an ultrasound probe or stereotactic apparatus, wherein the ultrasound probe or stereotactic apparatus is used to assist introduction of the solution into the tumor.

8. The method according to claim 1, wherein the tumor is located by means of a computed tomography or magnetic resonance scan.

9. The method according to claim 1, wherein the tumor is of a cancer selected from colorectal cancer, lung cancer, prostate cancer, breast cancer and brain cancer.

10. The method according to claim 1, wherein the step of introducing the solution is accompanied, preceded or followed by hormone ablation therapy.

* * * * *